US010828200B2

(12) United States Patent
Seo et al.

(10) Patent No.: US 10,828,200 B2
(45) Date of Patent: Nov. 10, 2020

(54) AUTOMATIC SHADING GOOGLES

(71) Applicant: SERVORE CO., LTD., Gyeonggi-do (KR)

(72) Inventors: Woon Su Seo, Gyeonggi-do (KR); Jeong Min Seo, Gyeonggi-do (KR)

(73) Assignee: SERVORE CO., LTD., Gyeonggi-Do (KR)

( * ) Notice: Subject to any disclaimer, the term of this patent is extended or adjusted under 35 U.S.C. 154(b) by 46 days.

(21) Appl. No.: 15/779,591

(22) PCT Filed: Jan. 13, 2016

(86) PCT No.: PCT/KR2016/000328
§ 371 (c)(1),
(2) Date: May 29, 2018

(87) PCT Pub. No.: WO2017/104890
PCT Pub. Date: Jun. 22, 2017

(65) Prior Publication Data
US 2019/0298574 A1    Oct. 3, 2019

(30) Foreign Application Priority Data
Dec. 17, 2015  (KR) .................. 10-2015-0180923

(51) Int. Cl.
*G02C 7/10*    (2006.01)
*A61F 9/06*    (2006.01)
(Continued)

(52) U.S. Cl.
CPC .................. *A61F 9/06* (2013.01); *A61F 9/04* (2013.01); *G02C 5/14* (2013.01); *G02C 7/10* (2013.01);
(Continued)

(58) Field of Classification Search
CPC .......... G02C 11/10; G02C 3/003; G02C 5/22; G02C 7/083; G02C 2200/08; G02C 11/12; G02C 5/08; G02C 9/00
(Continued)

(56) References Cited

U.S. PATENT DOCUMENTS 9,400,398 B2 *  7/2016  Darcy .................... G02C 5/146

FOREIGN PATENT DOCUMENTS

| JP | H09329770 | 12/1997 |
| KR | 10-2012-0093504 | 2/2011 |
| KR | 10-2012-0093504 | 8/2012 |

* cited by examiner

*Primary Examiner* — Hung X Dang
(74) *Attorney, Agent, or Firm* — IPLA P.A.; James E. Bame

(57) ABSTRACT

Automatic shading goggles that can be combined with fixing members, which can fix the goggles to the face of a wearer by separating end parts of foldable temples having a control module, includes: a goggle frame having front light-shield lenses and side light-shielding lenses; a skirt member detachably coupled inside the goggle frame to be brought in contact with the face of a wearer; and temples rotatably connected to the left and right of the goggle frame, respectively, and having a control module for controlling operation of the front light-shielding lenses, wherein the temples includes hinge parts having the control module and rotatably coupled to the left and right of the skirt member and earpieces separably coupled to ends of the hinge parts to be held on ears.

10 Claims, 4 Drawing Sheets

(51) Int. Cl.
  *G02C 5/14* (2006.01)
  *G02C 11/00* (2006.01)
  *G02C 13/00* (2006.01)
  *A61F 9/04* (2006.01)
  *G02C 9/00* (2006.01)

(52) U.S. Cl.
  CPC ............... *G02C 7/102* (2013.01); *G02C 9/00* (2013.01); *G02C 11/00* (2013.01); *G02C 11/12* (2013.01); *G02C 13/00* (2013.01); *G02C 13/001* (2013.01)

(58) Field of Classification Search
  USPC ........ 351/44, 116, 119, 153, 158; 2/12, 426, 2/427, 431, 432; 16/228
  See application file for complete search history.

AUTOMATIC SHADING GOOGLES

BACKGROUND

The present invention relates to goggles that automatically block harmful light and, more particularly, to automatic shading goggles that can be combined with fixing members, which can fix the goggles to the face of a wearer by separating end parts of foldable temples having a control module.

As is well known, automatic shading goggles block a harmful light generated during operation in industrial fields such as welding etc., thereby protecting a sense of sight and a face of a worker, a supervisor, or a medical practitioner using a laser. Recently, the automatic shading goggles capable of detecting the harmful light and automatically blocking it during generation thereof are widely used.

As a prior art related to the automatic shading goggles, "Automatic light-shielding goggles" (Korean patent No. 1285602; Registration date: Jul. 8, 2013) and "Detachable mask type automatic light-shielding goggles" (Korean patent No. 1482166; Registration date: Jan. 7, 2015) are disclosed.

In the prior art, when the harmful light is generated during operation thereof, a light sensing sensor detects the harmful light and outputs a driving signal and a control unit supplies a voltage to the light-shielding lens according to the driving signal inputted from the light sensing sensor, so that it drives the light-shielding lens according to a predetermined light-shielding degree.

However, in the conventional art, since it is fixed to a head through a band connected to both left and right sides of the body, there is a problem in that it is inconvenient for a worker or a supervisor to be worn and carried thereon. In other words, when working or overseeing during a short period of time, since the googles should be fixed to the head through the band, it is inconvenient to fix the goggles to the head. Also, it is not portable because it cannot be carried in a pocket etc. of clothing in a process of moving the goggles to the working place.

Moreover, the conventional art has a problem of poor usability because it cannot connect a bracket, which is connected to a safety helmet, or other fasteners such as a goggle leg thereto.

SUMMARY OF THE INVENTION

The present invention has been made in an effort to solve the above problem and an object of the present invention is to provide automatic shading goggles that can be combined with fixing members, which can fix the goggles to the face of a wearer by separating end parts of foldable temples having a control module so as to improve wearability and portability thereof.

According to one aspect of the present invention so as to accomplish these objects, there is provided to automatic shading goggles that automatically block harmful light, the goggles including: a goggle frame having front light-shield lenses and side light-shielding lenses; a skirt member detachably coupled inside the goggle frame to be brought in contact with the face of a wearer; and temples rotatably connected to the left and right of the goggle frame, respectively, and having a control module for controlling operation of the front light-shielding lenses, wherein the temples includes hinge parts having the control module and rotatably coupled to the left and right of the skirt member and earpieces separably coupled to ends of the hinge parts to be held on ears.

In the meantime, according to another aspect of the present invention so as to accomplish these objects, there is provided to automatic shading goggles that automatically block harmful light, the goggles including: a goggle frame having front light-shield lenses and side light-shielding lenses; a skirt member detachably coupled inside the goggle frame to be brought in contact with the face of a wearer; and temples rotatably connected to the left and right of the goggle frame, respectively, and having a control module for controlling operation of the front light-shielding lenses, wherein the temples includes hinge parts having the control module and rotatably coupled to the left and right of the skirt member and fixing members separably coupled to ends of the hinge parts to allow the goggles to fix to a head of the wearer.

According to the present invention, the skirt member includes a hard skirt frame and a soft skirt that are integrally formed by double-shot injection molding, and front lens fixing rims and side lens fixing rims are integrally formed on the skirt frame so as to fix the edges of the front light-shielding lenses and the side light-shielding lenses.

At this time, bosses having hinges are formed at both sides on the rear of the skirt frame, seats are formed in the front ends of the hinge parts so that the bosses are rotatably seated therein, and grooves are formed on the top and the bottom inside each of the seats to be rotatably coupled to hinges.

According to the present invention, fastening grooves are formed on the rear ends of the hinge parts and fastening protrusions, which are fitted in the fastening grooves, are formed on the front ends of the earpieces.

At this time, the fastening grooves include a fastening slit vertically formed at the rear end of the hinge part and a stopping groove formed wider than the fastening slit, and the fastening protrusions include fastening projections fitted in the fastening slits and stopping projections fitted in the stopping grooves so as to prevent separation of the fastening protrusion.

According to the present invention, fastening grooves are formed on the rear ends of the hinge parts and fastening protrusions, which are fitted in the fastening grooves, are formed on the front ends of the fixing member.

At this time, the fastening grooves include a fastening slit vertically formed at the rear end of the hinge part and a stopping groove formed wider than the fastening slit, and the fastening protrusions include fastening projections fitted in the fastening slits and stopping projections fitted in the stopping grooves so as to prevent separation of the fastening protrusion.

As described above, according to the present invention, there is an invaluable effect in that it can be conveniently carried and stored because the volume of a goggle member can be reduced by rotating temples and can be more conveniently used because earpieces or fixing members can be selectively fastened by separating end parts of the temples.

Also, according to the present invention, the skirt member is made of hard and soft materials through double-shot injection molding, so left-right or front-rear movement of the goggles in work can be minimized. Further, since bosses of the skirt member are disposed in seats of hinge parts and are not exposed to the outside, stable operation and aesthetic external appearance can be provided. Further, it is possible to prevent separation of earpieces or fixing members by fastening fastening grooves and fastening protrusions to each other.

BRIEF DESCRIPTION OF DRAWINGS

The above and other objects, features and advantages of the present invention will be more apparent from the following detailed description taken in conjunction with the accompanying drawings, in which.

DETAILED DESCRIPTION OF THE INVENTION

Figure 1:
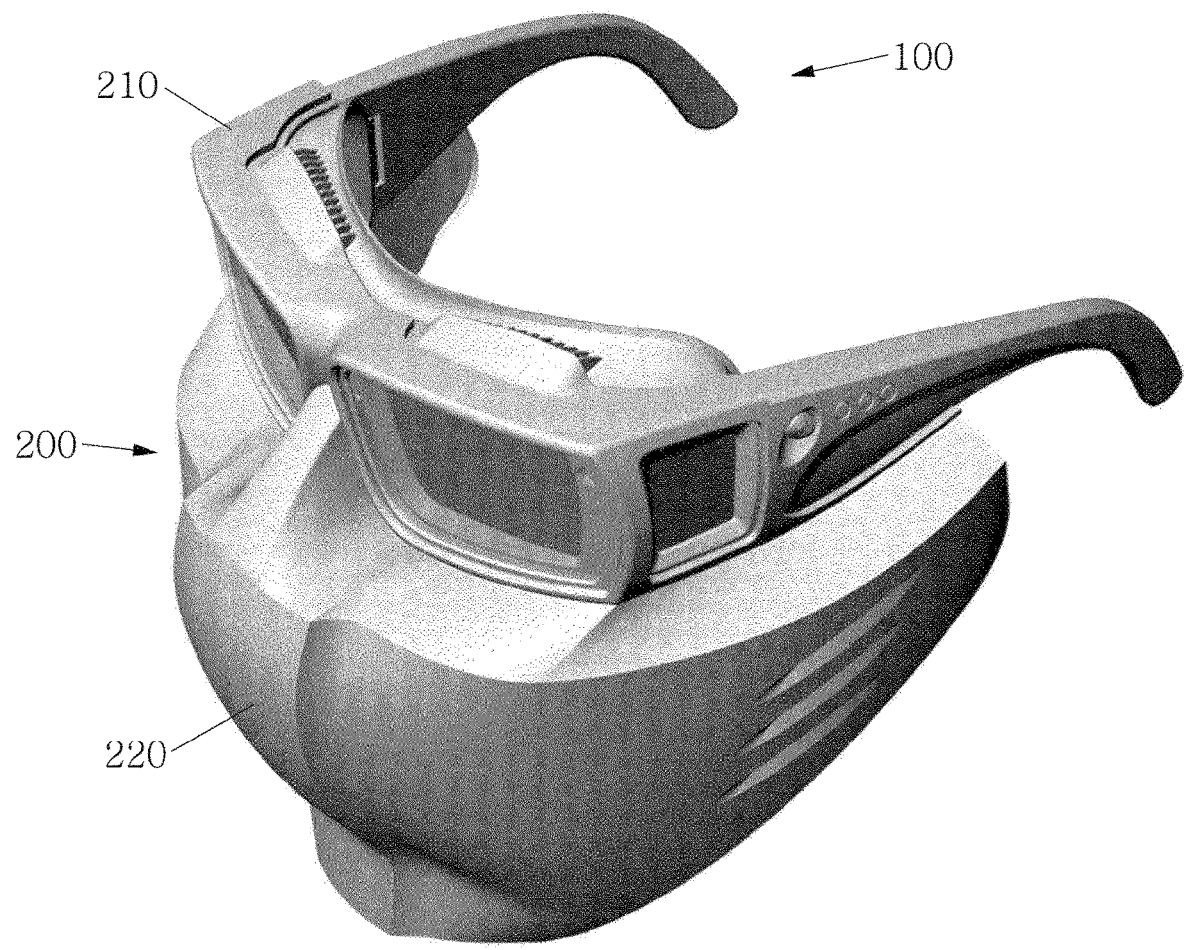
FIG. 1 is a perspective view of a state in which a goggle member and a mask member are coupled according to an embodiment of the present invention.

Hereinafter, in order to fully understand the present invention, exemplary embodiments of the present invention are described with reference to the accompanying drawings.

The present invention can be modified in various forms, and the scope of the present invention should not be interpreted as being limited to the embodiment described in detail below. The present invention is provided to more completely explain the present invention to those skilled in the art.

Accordingly, the shape and the like of the elements expressed in the drawings may be exaggerated in order to emphasize a clearer description. It should be noted that the same elements in each figure are denoted by the same reference numerals. In addition, detailed descriptions of well-known functions and configurations deemed to obscure the gist of the present invention are omitted.

Hereinafter, a preferred embodiment according to the present invention will be described in detail with reference to the accompanying drawings.

Figure 2:
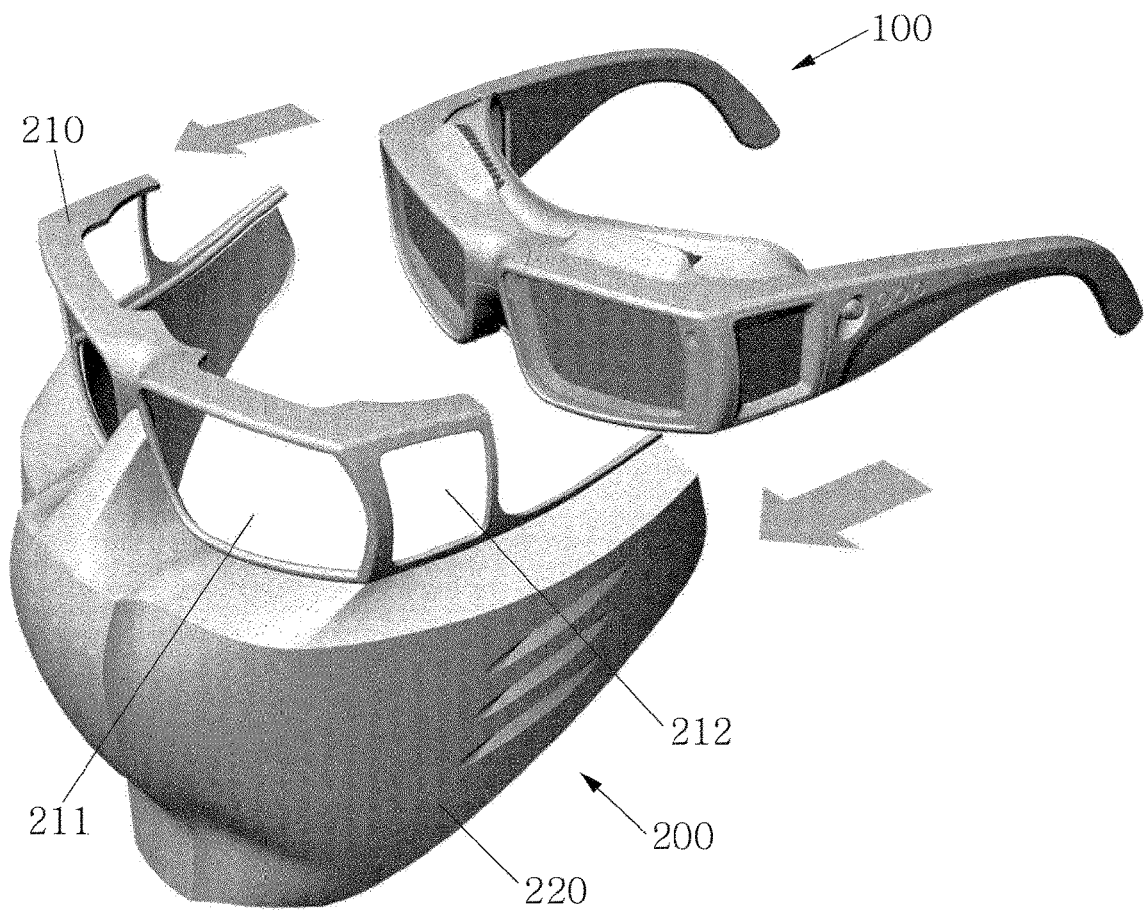
FIG. 2 is a perspective view of a state in which a security guard and a mask member are disassembled according to an embodiment of the present invention.

Automatic shading goggles of the present invention, as shown in FIGS. 1 and 2, largely includes: a goggle member (100) including a goggle frame (110) having light-shielding lenses (120 and 130), a skirt member (140) that is brought in contact with a face, and temples (150); and a mask member (200) including a bezel (210) for detachably coupling the goggle member (100) and a mask (220).

First, the goggle member (100) includes the goggle frame (110) having front light-shielding lenses (120) and side light-shielding lenses (130), the skirt member (140) detachably coupled to the inside of the goggle frame (110) to be brought in contact with the face of a wearer, and the temples (150) hinged to the left and right sides of the goggle frame (110), respectively, and having a control module for controlling operation of the front light-shielding lenses (120).

Figure 3:
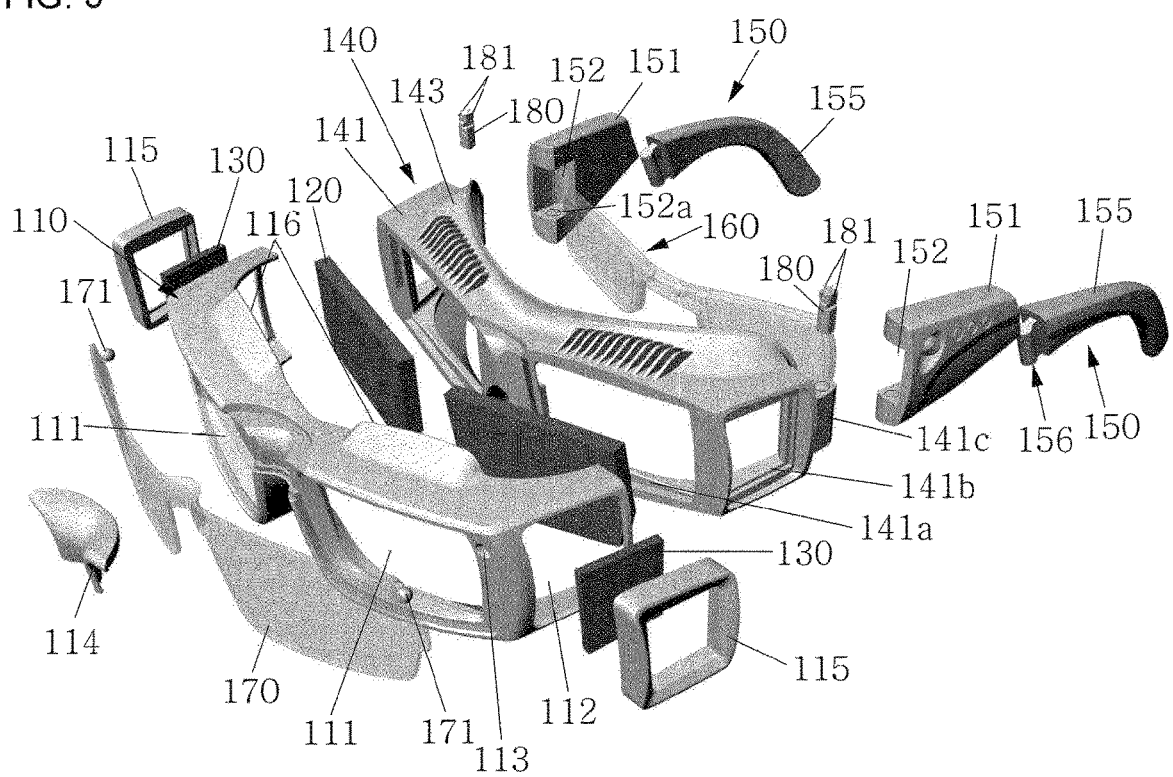
FIG. 3 is a perspective view of a state in which an essential portion of a goggle member is disassembled according to an embodiment of the present invention.

The goggle frame (110) forms the frame of the goggle member (100), and, as shown in FIG. 3, has front lens holes (111) at both sides of the front to couple the front light-shielding lenses (120) and side lens holes (112) at left and right sides to couple the side light-shielding lenses (130).

The front light-shielding lenses (120) are protected against damage due to fragments that is produced in work by a transparent protective lens (170) coupled to the front of the goggle frame (110).

The protective lens (170) has coupling protrusions (171) at both sides on the rear and the coupling protrusions (171) are fitted in coupling grooves (113) formed on the goggle frame (110). The protective lens (170) is firmly fixed by an end cap (114) fitted on the center of the upper end of the front of the goggle frame (110), thereby uniformly and aesthetically finishing the entire external appearance of the goggle frame (110).

The side light-shielding lenses (130) secure a wide side view angle that is visible to a wearer. The side light-shielding lenses (130) are colored lenses and firmly fixed by side lens rims (115).

Moisture exits (116) are formed at both sides on the top of the goggle frame (110) and discharges moisture produced inside the goggle frame (110) to the outside, thereby preventing the surfaces of the front light-shielding lenses (120) and the side light-shielding lenses (130) from being fogged.

The skirt member (140) is coupled inside the goggle frame (110) to be smoothly brought in contact with the face of a wearer. The skirt member (140) is composed of a hard skirt frame (141) and a soft skirt (143) that are integrally formed by double-shot injection molding.

The skirt frame (141) is made of hard and solid plastic materials and detachably coupled inside the goggle frame (110). Front lens fixing rims (141a) are formed at both sides of the front of the skirt frame (141) to firmly fix the edges of the front light-shielding lenses (120) and side lens fixing rims (141b) are formed on the left and right side of the skirt frame (141) to firmly fix the edges of the side light-shielding lenses (130). Bosses (141c) are formed at both sides on the rear of the skirt frame (141) to couple hinges (180) to be described below.

Further, elastic hooks (not shown) are formed at both sides of the front and/or on the upper and lower ends of the skirt frame (141) and hook grooves (not shown) are formed on the inner side of the goggle frame (110) to be elastically hooked to the elastic hooks, so the skirt frame (141) is detachably hooked to the inner side of the goggle frame (110).

Figure 6:
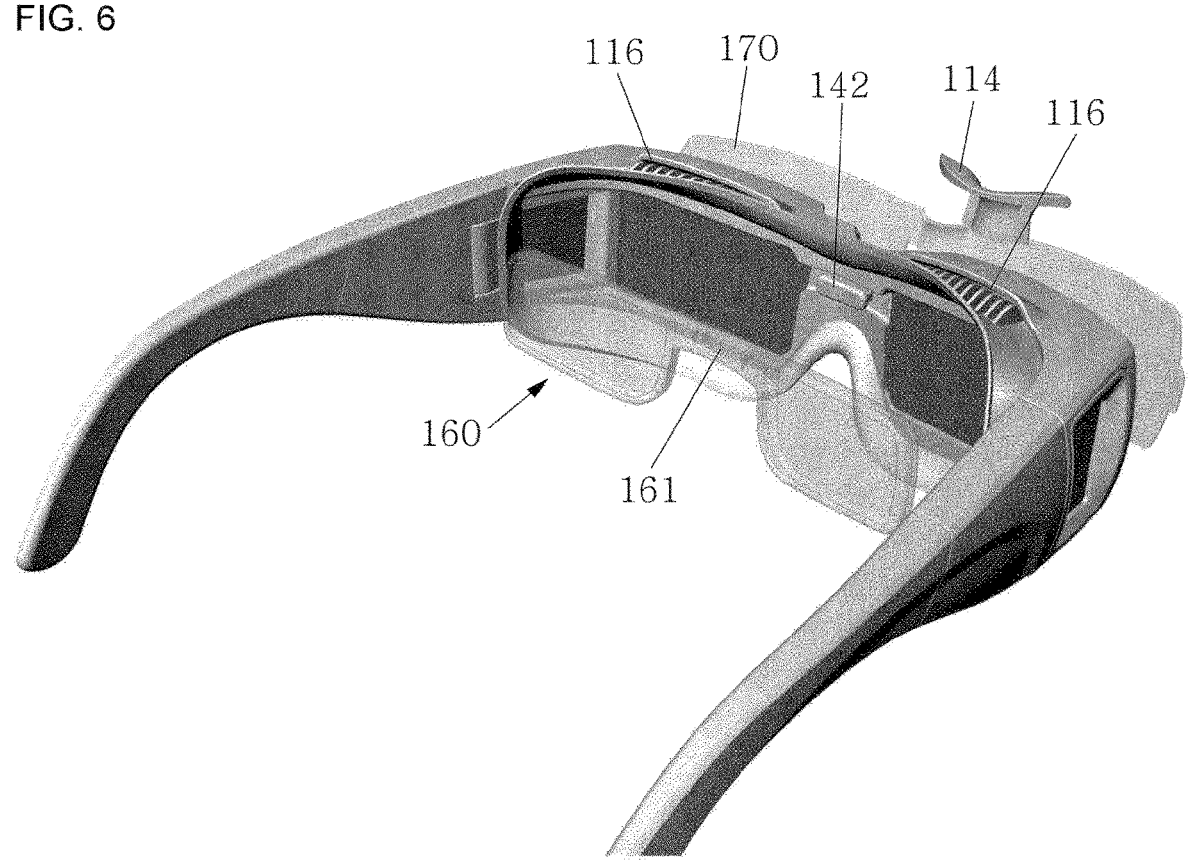
FIG. 6 is a perspective view of a state in which a glasses frame is disassembled from a goggle member according to an embodiment of the present invention.

Selectively, in order to detachably couple the skirt frame (141) to the inner side of the goggle frame (110), protrusions (not shown) may be formed at both sides and/or upper and lower ends of the skirt frame (141) and grooves (not shown) may be formed on the inner side of the goggle frame (110) to be fitted on the protrusions. Referring to FIG. 6, a fastening protrusion (142) is formed at the center of the inner side of the skirt frame (141), so glasses frame (160) for weak-eyed wearers can be detachably attached. To this end, a fastening groove (161) for detachably attaching the fastening protrusion (142) is formed on the glasses frame (160).

The skirt (143) is made of soft plastic material to be smoothly brought in contact with the face of a wearer, so it prevents noxious gas, etc. produced in work from flowing into the respiratory organs of a wearer.

The temples (150) are rotatably connected to the left and right of the skirt member (140) to be held on the ears of a wearer. The temples (150) have hinge parts (151) having a control module and rotatably connected to the left and right of the skirt member (140) and earpieces (155) separably coupled to the ends of the hinge parts (151) to be held on ears.

Figure 4:
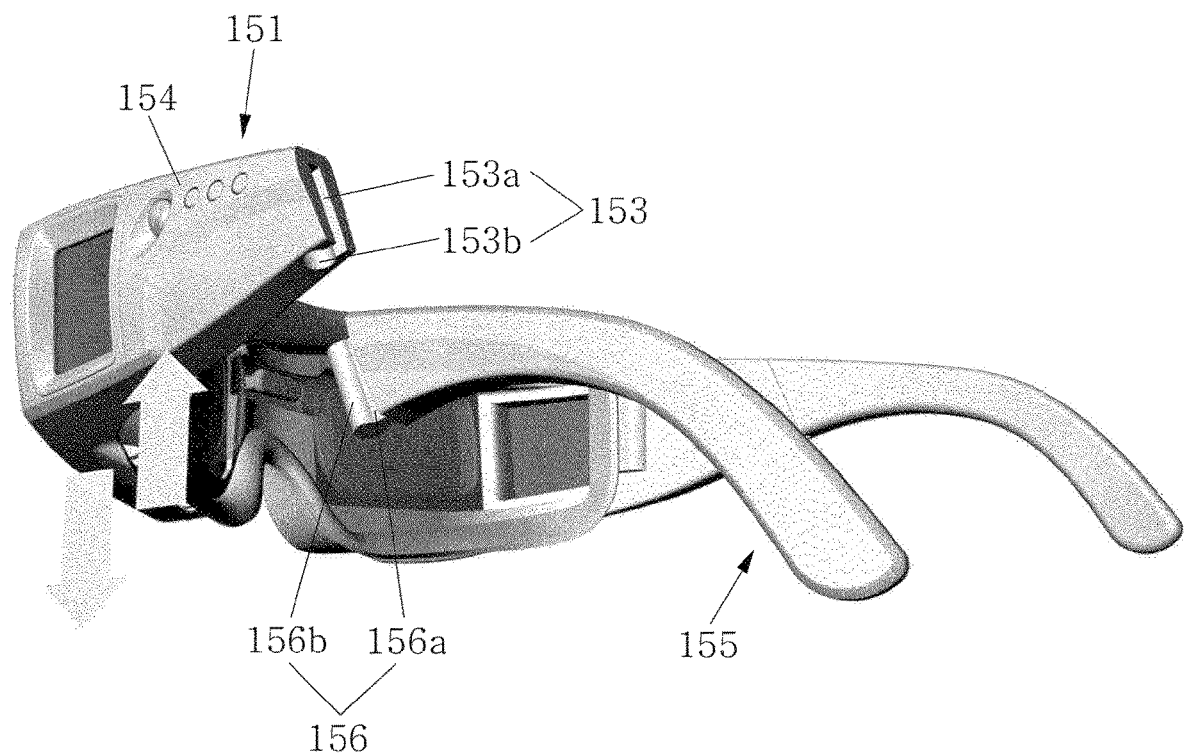
FIG. 4 is a perspective view of an exploded state of goggle temples according to an embodiment of the present invention.

Seats (152) are formed in the front ends of the hinge parts (151) so that the bosses (141c) of the skirt member (140) are rotatably seated therein. Hinge grooves (152a) are formed on the top and the bottom inside each of the seats (152) to be rotatably coupled to hinges (180) to be described below. Fastening grooves (153) are formed on the rear ends of the hinge parts (151) so that fastening protrusions (156) of the earpieces (155) to be described below are fitted therein. The fastening grooves (153), as shown in FIG. 4, each have a fastening slit (153a) vertically formed at the rear end of the hinge part (151) and a stopping groove (153b) formed wider than the fastening slit (153a) to prevent separation of the fastening protrusion (156).

The hinges (180), preferably, may be so-called step hinges that selectively control a rotational angle around 90°. Referring to FIG. 3, the hinge (180) has a groove or a flat stepped surface (181) having 90° at the upper external diameter thereof and a plate spring (not shown) is disposed in the hinge groove (152a) of the hinge part (151) to elastically restrict the stepped surface (181). Accordingly, when the hinge part (151) is rotated, it is stopped by the stepped surface (181) of the hinge (180), so the rotational angle is controlled around 90°.

A control module that controls operation of the front light-shielding lenses (120) is disposed at the hinge parts (151). The control module includes a power source (not shown) disposed at the left hinge part (151) and a control panel (154) disposed at the right hinge part (151). The power source is electrically connected to the front light-shielding lenses (120) and the control panel (154) to supply power.

The power source is preferably a secondary battery that can be replaced and charged. The control panel (154) controls the general operation of the front light-shielding lenses (120) in response to signals from a light sensor (not shown). The control panel (154) includes a control circuit board (not shown) electrically connected to the front light-shielding lenses (120) and the light sensor, and a light adjuster (not shown) electrically connected to the control circuit board to adjust the amount of light to be blocked by the front light-shielding lenses (120).

Various buttons and lamps are disposed on the outer side of the control panel (154) to show the states of power, light adjustment, and the battery.

The earpieces (155) are separably coupled to the rear ends of the hinge parts (151) to be held on ears. Fastening protrusions (156) are formed on the fronts of the earpieces (155) to be separably fitted in the fastening grooves (153) of the hinge parts (151). The fastening protrusions (156) have fastening projections (156a) fitted in the fastening slits (153a) of the fastening grooves (153) and stopping projections (156b) fitted in the stopping grooves (153b).

Accordingly, the fastening protrusions (156) of the earpieces (155) are fitted upward into the fastening grooves (153) of the hinge parts (151) and the earpieces (155) are held on ears, so the hinge parts (151) are not separated from the earpieces (155).

The mask member (200) includes a bezel (210) to which the goggle member (100) is detachably coupled and a mask (220) connected to the bottom of the bezel (210) to protect the face of a wearer.

The bezel (210), as shown in FIG. 2, is made of plastic material in a shape corresponding to the front and sides of the goggle member (100) and has front holes (211) formed at both sides of the front not to interfere with the visual fields of the front light-shielding lenses (120), and side holes (212) formed at left and right sides not to interfere with the visual fields of the side light-shielding lenses (130). Accordingly, the bezel (210) is combined with the goggle member (100) by elastically opening both sides.

The mask (220) covers and protects the face under the goggle member (100), that is, a nose, lips, and cheeks and both sides of the mask (220) extend to the hinge parts (151) of the temples (150), as shown in FIG. 1.

The operation of the present invention having this configuration is described in detail with reference to drawings.

First, as shown in FIG. 1, the goggle member (100) can be coupled and used with the mask member (200). That is, as shown in FIG. 2, when the front and sides of the goggle member are pushed inside the bezel (210), both sides of the bezel (210) are slightly opened for the characteristic of the material and is coupled to the goggle member (100). Accordingly, not only the eyes, but the face under the eyes of a wearer can be protected.

Further, as shown in FIG. 4, various fixing members can be connected by separating or fastening the earpieces (155). That is, the earpieces (155) having the fastening protrusions (156) are fastened to the hinge parts (151) and held on ears, thereby fixing the goggles of the present invention.

If necessary, a headband (not shown) having the fastening protrusions (156) at both ends to be elastically fixed around the head of a wearer or a bracket (not shown) having fastening protrusions to be coupled to the lower ends of two sides of a helmet may be used to fix the goggles of the present invention.

Figure 5:
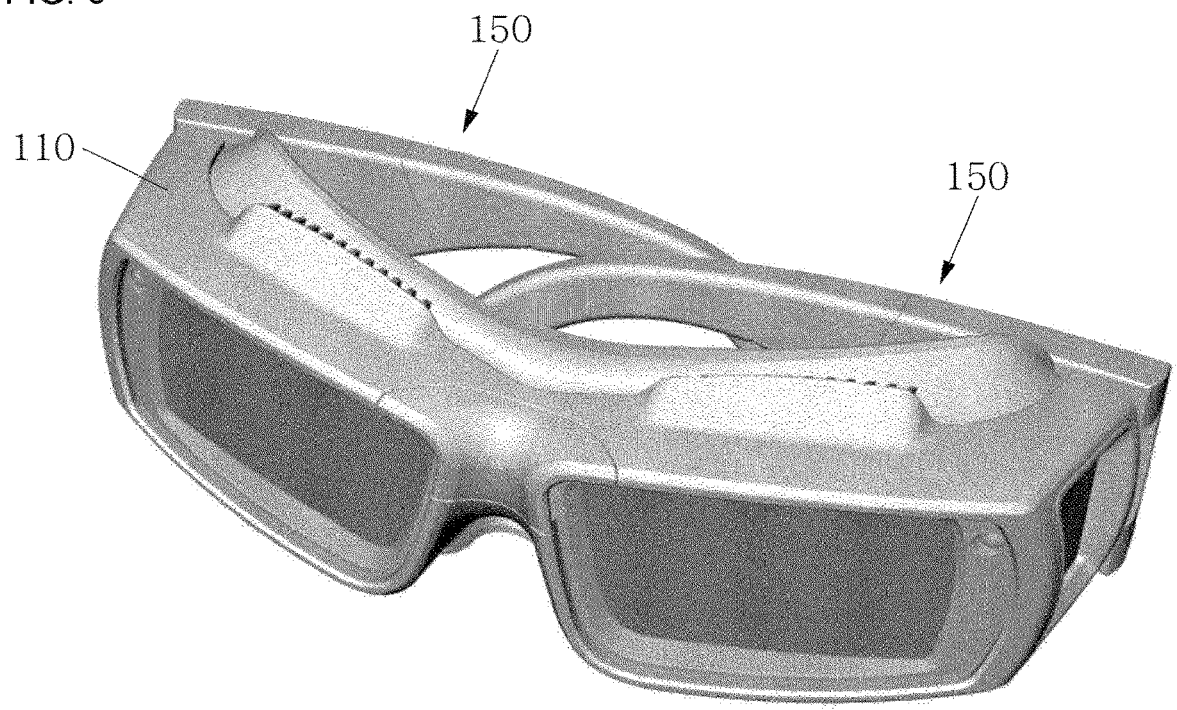
FIG. 5 is a perspective view of a state of folding goggle temples according to an embodiment of the present invention.

Further, as shown in FIG. 5, the goggles can be more conveniently carried and stored by folding the temples (150) inside the skirt member (140). That is, since the rotational angle of the temples (150) is selectively restricted around 90° by the hinges (180), when the hinge parts (151) are rotated inside toward the skirt member (140), the temples (150) are maintained at a folded or unfolded position without easily rotating unless the hinge parts (151) is rotated by a predetermined force. Accordingly, it is possible to easily carry the goggles of the present invention with the temples (150) inserted in a pocket of clothes.

Further, as shown in FIG. 6, weak-eyed wearers use the goggles of the present invention with the glasses frame (160) coupled inside the skirt frame (141), workability and efficiency are improved.

While the present invention has been described with respect to the specific embodiments described above, it will be apparent to those skilled in the art that various changes and modifications may be made without departing from the spirit and scope of the present invention as defined in the following claims.

Therefore, it is to be understood that the present invention is not limited to the forms mentioned in the above detailed description.

Therefore, it is intended that the present invention cover the modifications and variations of this invention provided they come within the scope of the appended claims and their equivalents. Furthermore, it is intended that the present invention cover all modifications, equivalents and alternatives falling within the spirit and scope of the invention as defined by the appended claims.

The invention claimed is:

1. Automatic shading goggles that automatically block harmful light, the goggles comprising:
a goggle frame having front light-shield lenses and side light-shielding lenses;

a skirt member detachably coupled inside the goggle frame to be brought in contact with the face of a wearer; and temples rotatably connected to the left and right of the goggle frame, respectively, and having a control module for controlling operation of the front light-shielding lenses, wherein the temples includes hinge parts having the control module and rotatably coupled to the left and right of the skirt member and earpieces separably coupled to ends of the hinge parts to be held on ears.

2. The automatic shading goggles as claimed in claim 1, wherein the skirt member includes a hard skirt frame and a soft skirt that are integrally formed by double-shot injection molding, and front lens fixing rims and side lens fixing rims are integrally formed on the skirt frame so as to fix the edges of the front light-shielding lenses and the side light-shielding lenses.

3. The automatic shading goggles as claimed in claim 2, wherein bosses having hinges are formed at both sides on the rear of the skirt frame, seats are formed in the front ends of the hinge parts so that the bosses are rotatably seated therein, and grooves are formed on the top and the bottom inside each of the seats to be rotatably coupled to the hinges.

4. The automatic shading goggles as claimed in claim 1, wherein fastening grooves are formed on the rear ends of the hinge parts and fastening protrusions, which are fitted in the fastening grooves, are formed on the front ends of the earpieces.

5. The automatic shading goggles as claimed in claim 4, wherein the fastening grooves include a fastening slit vertically formed at the rear end of the hinge part and a stopping groove formed wider than the fastening slit, and the fastening protrusions include fastening projections fitted in the fastening slits and stopping projections fitted in the stopping grooves so as to prevent separation of the fastening protrusion.

6. Automatic shading goggles that automatically block harmful light, the goggles comprising:

a goggle frame having front light-shield lenses and side light-shielding lenses;

a skirt member detachably coupled inside the goggle frame to be brought in contact with the face of a wearer; and temples rotatably connected to the left and right of the goggle frame, respectively, and having a control module for controlling operation of the front light-shielding lenses, wherein the temples includes hinge parts having the control module and rotatably coupled to the left and right of the skirt member and fixing members separably coupled to ends of the hinge parts to allow the goggles to fix to a head of the wearer.

7. The automatic shading goggles as claimed in claim 6, wherein the skirt member includes a hard skirt frame and a soft skirt that are integrally formed by double-shot injection molding, and front lens fixing rims and side lens fixing rims are integrally formed on the skirt frame so as to fix the edges of the front light-shielding lenses and the side light-shielding lenses.

8. The automatic shading goggles as claimed in claim 7, wherein bosses having hinges are formed at both sides on the rear of the skirt frame, seats are formed in the front ends of the hinge parts so that the bosses are rotatably seated therein, and grooves are formed on the top and the bottom inside each of the seats to be rotatably coupled to the hinges.

9. The automatic shading goggles as claimed in claim 6, wherein fastening grooves are formed on the rear ends of the hinge parts and fastening protrusions, which are fitted in the fastening grooves, are formed on the front ends of the fixing member.

10. The automatic shading goggles as claimed in claim 9, wherein the fastening grooves include a fastening slit vertically formed at the rear end of the hinge part and a stopping groove formed wider than the fastening slit, and the fastening protrusions include fastening projections fitted in the fastening slits and stopping projections fitted in the stopping grooves so as to prevent separation of the fastening protrusion.

\* \* \* \* \*